United States Patent [19]

Tiedge et al.

[11] Patent Number: 5,670,318
[45] Date of Patent: Sep. 23, 1997

[54] HUMAN BC200 RNA PROBES AND A METHOD OF SCREENING FOR BREAST CANCER USING THE PROBES THEREFOR

[75] Inventors: Henri Tiedge; Jurgen Brosius, both of New York, N.Y.

[73] Assignee: Reel 6624, Frame 0438-Mount Sinai School of Medicine of the City of New York, New York, N.Y.

[21] Appl. No.: 438,500

[22] Filed: May 10, 1995

Related U.S. Application Data

[63] Continuation of Ser. No. 68,659, May 28, 1993, abandoned.

[51] Int. Cl.$^6$ .................. C12Q 1/68; C07H 21/04
[52] U.S. Cl. .................. 435/6; 536/24.31; 536/24.33; 935/77; 935/78
[58] Field of Search .................. 536/24.31; 435/6, 435/91.2, 91.1, 91.51; 935/77, 78

[56] References Cited

U.S. PATENT DOCUMENTS

| | | | |
|---|---|---|---|
| 4,486,539 | 12/1984 | Ranki et al. | 435/6 |
| 4,683,202 | 7/1987 | Mullis | 435/91.2 |
| 4,751,177 | 6/1988 | Stabinsky | 435/6 |
| 4,868,105 | 9/1989 | Urdea et al. | 435/6 |
| 4,894,325 | 1/1990 | Englehardt et al. | 435/6 |

FOREIGN PATENT DOCUMENTS 0238332 of 0000 European Pat. Off. .

OTHER PUBLICATIONS

J.B. Watson and J.G. Sutcliffe, Molecular and Cellular Biology, *Primate Brain–Specific Cytoplasmic Transcript of the Alu Repeat Family*, Sep. 1987, pp. 3324–3327.

K.A. Kelley et al., Genomics 13, *Expression and Chromosome Localization of the Murine Cystic Fibrosis Transmembrane Conductance Regulator*, Jan. 9, 1992, pp. 381–388.

Francis Barany, Proc. Natl. Acad. Sci. USA, *Genetic Disease Detection and DNA Amplification Using Cloned Thermostable Ligase*, Jan. 1991, pp. 189–193.

D.Y. Kwoh et al., Proc. Natl. Acad. Sci. USA, *Transcription–based Amplification System and Detection of Amplified Human Immunodeficiency Virus Type 1 With a Bead–based sandwich Hybridization Format*, Feb. 1989, vol. 86, pp. 1173–1177.

T. Uchiumi et al., The Journal of Biological Chemistry, *A Human Autoantibody Specific for a Unique Conserved Region of 28 S Ribosomal RNA Inhibits the Interaction of Elongation Factors 1α and 2 With Ribosomes*, Feb. 5, 1991, vol. 266, No. 4, pp. 2054–2062.

J.C. Hanvey et al., Science, *Antisense and Antigens Properties of Peptide Nucleic Acids*, Nov. 27, 1992, vol. 258, pp. 1481–1485.

J.R. Feramisco et al., The Journal of Biological Chemistry, *Co–existence of Vinculin and a Vinculin–like Protein of Higher Molecular Weight in Smooth Muscle*, Sep. 25, 1982, vol. 257, pp. 11024–11031.

T.M. DeChiara and J. Brosius, Proc. Natl. Acad. Sci. USA, *Neural BC1 RNA:cDNA Clones Reveal Nonrepetitive Sequence Content*, May 1987, Proc. Natl. Acad. Sci. USA, vol. 84, pp. 2624–2628.

H. Tiedge et al., Proc. Natl. Acad. Sci. USA, *Dendritic Location of Neural BC1 RNA*, Mar. 1991, vol. 88, pp. 2093–2097.

F. Sanger et al., Proc. Natl. Acad. Sci. USA, *DNA Sequencing with Chain–terminating Inhibitors*, Dec. 1977, vol. 74, No. 12, pp. 5463–5467.

F. Toneguzzo et al., BioTechniques(Research Report), *Use of Chemically Modified T7 DNA Polymerase for Manual and Automated Sequencing of Supercoiled DNA*, 1988, vol. 6, No. 5, pp. 460–469.

M.A. Frohman et al., Proc. Natl. Acad. Sci. USA, *Rapid Production of Full–length cDNAs From Rare Transcripts: Amplification Using a Single Gene–specific Oligonucleotide Primer*, Dec. 1988, vol. 85, pp. 8998–9002.

W.J. Luwik et al., Neurochemical Research, *BC200 RNA in Normal Human Neocortex, Non–Alzeheimer Dementia (NAD), and Senile Dementia of the Alzheimer Type (AD)*, 1992, vol. 17, No. 6, pp. 591–597.

T. Giordano et al., Mechanisms of Ageing and Development, *Expression of Alu and 7SL RNA in Alzheimer's and Control Brains*, 1992, vol. 64, pp. 13–20.

H. Tiedge et al., The Journal of Neuroscience, *Primary Structure, Neural–Specific Expression, and Dendritic Location of Human BC200 RNA*, Jun. 1993, vol. 13(6), pp. 2382–2390.

Martignetti, Dissertation Abstract, vol. 53/10–B of Dissertation Abstracts International, p. 5080 (1992).

Stratagene 1988 Catalog, p. 39.

Guttman et. al., J. of Chromatography 593: 297–303 (1992).

*Primary Examiner*—Lisa B. Arthur
*Attorney, Agent, or Firm*—Brumbaugh, Graves, Donohue & Raymond

[57] ABSTRACT

The 3'-end of BC200 RNA, commencing at nucleotide 159 has the sequence:

UAAGCGUAAC UUCCCUCAAA GCAACAACCC CCCCCCCCCU UU 42  [SEQ ID NO 2]

Oligonucleotide probes in accordance with the invention are complementary to at least a portion of this sequence such that they bind specifically and selectively to human BC200 RNA. The probes are useful for screening human breast tissue for the presence of adenocarcinoma.

8 Claims, 1 Drawing Sheet

HUMAN BC200 RNA PROBES AND A METHOD OF SCREENING FOR BREAST CANCER USING THE PROBES THEREFOR

This patent application is a continuation of U.S. patent application Ser. No. 08/068,659, filed May 28, 1993, now abandoned.

SPECIFICATION

The invention described in this application was made with funding provided by the National Institute of Mental Health under grant number MH38819. The United States may have certain rights to the invention.

BACKGROUND OF THE INVENTION

This application relates to oligonucleotide probes that are specific for human BC200 RNA and to the use of these probes in screening for neoplastic diseases and neurological and psychiatric disorders.

BC200 RNA is a 200-nucleotide long, non-translatable RNA that is prevalently expressed in the nervous system of primates, including man. A partial nucleotide sequence of BC200 RNA from monkey brains was reported by Watson and Sutcliffe, Molecular & Cellular Biology 7, 3324–3327 (1987). This 138 nucleotide sequence showed substantial homology to the Alu left monomer, a sequence that is repeated many times throughout the human and other primate genomes. Watson and Sutcliffe hypothesized that the remainder of the 200-nucleotide RNA may correspond to a poly-(A) tract.

We have now determined the complete sequence for human BC200 RNA and have discovered that the 3'-end of the polynucleotide includes a unique sequence which can be used to specifically detect the presence of human BC200 RNA without interference from other instances of the Alu sequence within the genome. Further, we have discovered that while BC200 RNA does not appear to occur in detectable amounts in normal non-neuronal tissue other than germ cells, it does occur consistently in high amounts in a variety of non-neuronal human tumor tissues.

Accordingly, it is an object of the present invention to provide oligonucleotide probes that bind specifically with the unique portion of human BC200 RNA or a corresponding chromosomal DNA sequence.

It is a further object of the present invention to provide a method to test for the presence of BC200 RNA in a tissue sample, particularly for purposes of screening for neoplastic diseases and neurological and psychiatric disorders.

It is a further object of the present invention to provide kits useful in testing for the presence of BC200 RNA in a tissue sample.

SUMMARY OF THE INVENTION

The 3'-end of BC200 RNA, commencing at nucleotide 159 has the sequence:

UAAGCGUAAC UUCCCUCAAA GCAACAACCC CCCCCCCCCU UU 42    [SEQ ID NO 2]

Oligonucleotide probes in accordance with the invention are complementary to at least a portion of this sequence such that they bind specifically and selectively to human BC200 RNA. The probes are useful in determining the distribution of BC200 RNA in the body and as an indicator of neoplastic diseases in non-neuronal tissue. In addition, probes spanning nucleotides 48 and 49 or the non-A nucleotides of the A-rich region (146–148) of BC200 RNA are useful for detecting the RNA.

DETAILED DESCRIPTION OF THE INVENTION

Primate BC200 RNA is a 200-nucleotide long non-translatable RNA. We have determined the primary sequence of human BC200 RNA to be as follows:

```
XXCCGGGCGC GGUGGCUCAC GCCUGUAAUC CCAGCUCUCA GGGAGGCUAA GAGGCGGGAG  60   [SEQ ID NO 1]
GAUAGCUUGA GCCCAGGAGU UCGAGACCUG CCUGGGCAAU AUAGCGAGAC CCCGUUCUCC 120
AGAAAAAGGA AAAAAAAAAA CAAAAGACAA AAAAAAAAUA AGCGUAACUU CCCUCAAAGC 180
AACAACCCCC CCCCCCUUU                                              200
```

The X's at positions 1 and 2 are independently either G or absent.

This primary sequence can be subdivided into three structural domains. Domain I is nucleotides 1–122 and is substantially homologous to Alu repetitive elements which are found in high copy numbers in primate genomes. However, this region includes two bases not found in Alu or SRP-RNA, i.e., nucleotides at positions 48 and 49, which can be used to develop amplification primers specific to BC200 sequences. Domain II is an A-rich region consisting of nucleotides 123–158. Domain III, consisting of nucleotides 159–200, contains a unique sequence, with no homology to other known human sequences, which can be used to identify BC200 RNA in tissues.

In one aspect of the present invention, oligonucleotide probes are provided which are complementary to the unique sequences of Domain III of human BC200 RNA, or to corresponding chromosomal DNA, i.e., which are complementary to at least a portion of the sequence:

UAAGCGUAAC UUCCCUCAAA GCAACAACCC    [SEQ ID NO 2]
CCCCCCCCU UU 42

Such probes are linear oligonucleotides containing from about 10 to 60 bases. The length must be sufficient to provide a reasonable degree of specificity such that binding with BC200 RNA will be preferred over binding to other polynucleotides.

As used herein, the term "oligonucleotide probe" refers to either a DNA or an RNA probe.

One probe within the scope of the invention is complementary to the nucleotides 156-185 of BC200 RNA. This 30-nucleotide probe has the sequence:

TTGTTGCTTT GAGGGAGTT ACGCTTATTT 30     [SEQ ID NO 3]

Another useful probe is a 21-nucleotide probe complementary to nucleotides 158-178, i.e.:

TTTGAGGGAA GTTACGCTTA T 21     [SEQ ID NO 7]

As will be apparent from these two examples, suitable probes may be complementary with the portions of BC200 RNA outside Domain III, provided they are also complementary to a portion (i.e., at least about 10 bases) of the unique Domain III sufficient to provide specificity. Probes may also be complementary to portions of Domain III alone. A further aspect of the invention is a second class of probes which are complementary to a portion of Domain II spanning nucleotides 146-148. These probes may be used for detection of BC200 RNA or as amplification primers.

In a still further aspect of the invention, probes can be utilized which are complementary to and specifically hybridize with a portion of the Alu-repetitive sequence spanning the two unique nucleotides at positions 48 and 49 of BC200 RNA or corresponding DNA. Examples of such probes are:

CCTCTTAGCC TCCCTGAGAG CT 22     [SEQ ID NO 12]

an antisense probe that will bind BC200 RNA and:

CCAGCTCTCA GGGAGGCTAA 20     [SEQ ID NO 13]

a sense probe that will bind to corresponding DNA sequences. These probes can be used for detection or as amplification primers.

The probes of the present invention can be made by any of a variety of techniques known in the art. For example, RNA probes can be generated by in vitro transcription. In this approach, the desired sequence is first cloned into a suitable transcription vector (e.g., pBluescript). This vector is linearized so that transcription will terminate at a specific location, and RNA is transcribed from such linearized templates, using SP6, T3, or T7 RNA polymerase. The probes can be $^{35}$S- or $^3$H-labeled by adding the appropriate radiolabeled precursors to the reaction mixture. Template DNA is then digested with DNase I. RNA probes can be further purified by gel filtration or gel electrophoresis.

Probes can also be made by oligolabeling, although this technique is more suited to longer nucleic acid polymers. In this method, double stranded DNA is first denatured. Random sequence oligonucleotides are then used as primers for the template directed synthesis of DNA. The Klenow fragment of E. coli DNA polymerase I is frequently used in this application. Reverse transcriptase can be used if the template is RNA. Labeling of the probe is achieved by incorporation of radiolabeled nucleotides, e.g., [α-$^{32}$P]dNTps.

Another approach for generation of probes is nick translation. Double stranded DNA is used in this method. Nicks (gaps in one strand) are introduced by DNase I. E. coli DNA polymerase I is used simultaneously to add nucleotide residues to the 3' termini of the DNA at the nick points. Incorporation of radiolabeled precursor nucleotides results in the uniform labeling of the probe. Probes contain both strands.

Single stranded DNA probes can be made from templates derived from bacteriophage M13 or similar vectors. An oligonucleotide primer, complementary to a specific segment of the template, is then used with the Klenow fragment of E. coli DNA polymerase I to generate a radiolabeled strand complementary to the template. The probe is purified for example by gel electrophoresis under denaturing conditions.

Oligonucleotides of any desired sequence can also be synthesized chemically. Solid phase methods are routinely used in the automated synthesis of oligonucleotides.

Probes useful in the invention can be labeled. A variety of enzymes can be used to attach radiolabels (using dNTP precursors) to DNA termini. The 3' termini of double stranded DNA can for example be labeled by using the Klenow fragment of E. coli DNA polymerase I. Blunt ended DNA or recessed 3' termini are appropriate substrates. T4 DNA polymerase can also be used to label protruding 3' ends. T4 polynucleotide kinase can be used to transfer a $^{32}$P-phosphate group to the 5' termini of DNA. This reaction is particularly useful to label single stranded oligonucleotides. Probes can also be labeled via PCR labeling in which labeled nucleic acids and/or labeled primers are used in PCR generation of probes from an appropriate clone. See Kelly et al., Genomics 13: 381-388 (1992).

The probes of the invention can be used to screen tissue for the presence of BC200 RNA. For example, the distribution of BC200 RNA in the human retina was determined, with the result that BC200 RNA was detected in the ganglion cell layer, the inner plexiform layer and the innermost layer of the inner nuclear layer but not in other parts of the retina. Similar mapping was possible in the hippocampus and neocortex using the probes of the invention.

Using the aforementioned probes in in situ hybridization experiments, we have demonstrated that BC200 expression levels are altered in some brain areas of aging individuals and in Alzheimer's brains. In several cortical areas, specifically Brodmann areas 9 and 17/18, BC200 levels were found to decrease with age (age group 50-90 years). In the same brain areas of Alzheimer's patients, a drastic increase of BC200 expression was observed. BC200 probes can therefore be used to differentiate between Alzheimer's disease and normal aging.

Non-neuronal tissues may also be tested for the presence of BC200 RNA in accordance with the invention. We have observed that most normal, non-neuronal tissue does not contain detectable amounts of BC200 RNA, but that a variety of human tumor tissues do express BC200 RNA which can be detected using the probes of the invention. Thus, a further aspect of the invention is a method of screening for neoplastic diseases using probes for BC200 RNA.

The basic methodology of the screening procedure involves the following steps:

(1) obtaining a physiological sample;
(2) treating the sample to render RNA and/or DNA available for hybridization;
(3) hybridizing the treated sample with a probe specific for Domain III of human BC200 RNA; and
(4) analyzing for the occurrence of hybridization. Suitable physiological samples include biopsy specimens, body fluids such as sputum, cervical or esophagal scrapings and skin samples. Neuronal tissue, for example biopsy specimens and post-mortem material, may also be screened for BC200 RNA for assessment of neurological disorders.

While the method employed to treat the tissue sample is not critical, provided that nucleic acids in the sample are made available for hybridization, several specific options are worth noting. Direct isolation of RNA by the guanidine thiocyanate method followed by CsCl-density gradient centrifugation may be effective in many cases, particularly for isolation of RNA from biopsy specimens. (See Example 4) Where the sample size is small, as in a sputum sample for example, however, amplification of the RNA may be desirable.

Amplification of the RNA can be achieved by first lysing cells in the sample to render RNA available for hybridization. This can be accomplished by (1) extraction of RNA with guanidinium thiocyanate, followed by centrifugation in cesium chloride; (2) extraction of RNA with guanidine HCl and organic solvents; or (3) extraction of RNA with mild detergents (such as NP-40), combined with proteinase digestion. These and other RNA extraction methods are described in Sambrook et al. The isolated RNA is converted into cDNA which is then amplified using probes selective for the 3' end of BC200 sequence. (See Example 3 and U.S. Pat. No. 4,683,202 incorporated herein by reference.) cDNA may also be amplified using ligase-based methods (Barany et al., Proc. Nat'l. Acad. Sci. USA 88, 189–193 (1991)) or isothermal transcription-based methods (Kwoh et al., Proc. Nat'l. Acad. Sci. USA 86, 1173–1177 (1989)). The amplified DNA can then be detected directly via an appropriate probe in accordance with the invention.

The hybridization can be carried out using any of the numerous procedures known for assaying for nucleic acids. These include various blot techniques (i.e., dot, Northern, Southern, etc.), and sandwich based techniques such as those described in U.S. Pat. Nos. 4,486,539; 4,751,177; 4,868,105; 4,894,325 and European Patent Publication 0 238 332 (all of which are incorporated herein by reference). To facilitate detection, the probe may have a label, such as a radiolabel, chemiluminescent label, fluorescent label or chromogenic label, or an immobilization moiety. Probes modified with biotin or digoxygenin, which can serve as either a detectable label or an immobilization moiety, are particularly useful.

The probes of the invention are suitably supplied as part of a kit for screening tissue for BC200 RNA. In addition to the probe or other detection reagent that produces a diagnostic reaction product if BC200 RNA is present, such a kit may include one or more of the following:

(1) a solid support to which the diagnostic reaction product nucleic is affixed during the screening procedure;

(2) amplification primers and enzymes for amplification of nucleic acids in a sample;

(3) a labeled reagent that reacts with the diagnostic reaction product to render it detectable; and (4) solutions effective to lyse the physiological sample to render RNA available for hybridization. Suitable amplification primers include those identified in Example 2, as well as others which will result in amplification, if present, of Domain III of BC200 RNA, possibly together with portions of Domains II and I. A particularly preferred 5'-amplification primer is one that is complementary to a portion of Domain I of BC200 RNA, or the corresponding cDNA, that includes the unique nucleotides at positions 48 and 49. Suitable enzymes include reverse transcriptase, Taq polymerase, rTth DNA polymerase and RNA polymerase.

While the invention is described principally in terms of using oligonucleotide hybridization probes to detect BC200 RNA, it will be appreciated that the beneficial result of screening for neoplastic diseases can be achieved using any detection technique. For example, RNA-specific antibodies to BC200 RNA could be used, e.g., in an ELISA assay, to detect BC200 RNA in tissue samples. See Uchiumi et al., J. Biol. Chem. 266: 2054–62 (1991). Peptide nucleic acids that hybridize with BC200 RNA may also be used as diagnostic reagents. See Hanvey et al., Science 258: 1481–1485 (1992). Similarly, we have observed that BC200 RNA may be complexed with proteins in vivo to form a ribonucleoprotein ("RNP"). Antibodies specific to BC200-RNP could also be used in an immunoassay detection scheme.

EXAMPLE 1

Determination of Human BC200 RNA Sequence

Total cellular RNA and poly(A)$^+$ RNA were isolated from human neocortex according to the method of Feramisco et al., J. Biol. Chem. 257: 11024–11031 (1982). 5 µg of poly(A)$^+$ RNA were tailed with CTP, using poly A polymerase, and the C-tailed RNA was converted into double-stranded cDNA as described in DeChiara et al., Proc. Nat'l. Acad. Sci. USA 84: 2624–2628 (1987). EcoRI-adaptors (Pharmacia) were attached, according to the instructions of the manufacturer, and cDNA smaller than about 400 base pairs was selected on a 4% polyacrylamide gel. Electro-eluted cDNA was cloned into λZAP (Stratagene), following the manufacturer's manual. We screened $3.6 \times 10^4$ plaques with an oligonucleotide probe complementary to the sixty 3'-most nucleotides of rat BC1 RNA (DeChiara et al., 1987; Tiedge et al., Proc. Nat'l. Acad. Sci. USA 88: 2093–2097 (1991)) at low stringency (final wash at 35° C. in 6×SSC; 1×SSC is 150 mM sodium chloride, 15 mM sodium citrate, pH 7.4). Four clones were identified as positive, and the sequences of their inserts (both strands) were determined using the enzymatic chain termination reaction. Sanger et al., Proc. Nat'l. Acad. Sci. USA 74: 5463–5467 (1977); Toneguzzo et al., Biotechniques 6: 460–469 (1988). Twelve additional clones were later identified and sequenced using the enzymatic chain termination method after rescreening of the library with oligonucleotide probes complementary to specific BC200 RNA sequences, and yielded additional information about Domain I. The resulting sequence based on all of the clones is shown above (SEQ ID NO 1).

EXAMPLE 2

Amplification of BC200 RNA

The 5' and 3' Domains of BC200 RNA were amplified separately.

For amplification of the 5' BC200 sequence, 1 µg total RNA was isolated from human neocortex using the guanidinium thiocyanate method followed by phenol extraction and CsCl centrifugation, and converted into first strand cDNA using the thermostable rTth DNA polymerase (Perkin Elmer Cetus) according to the instructions of the manufacturer. The primer used in this step was GTTGTTGCTT TGAGGGAAG 19     [SEQ ID NO 4]

The 3' end of the product was then T-tailed using dTTP and terminal transferase (Boehringer Mannheim). The tailed cDNA was PCR-amplified (Frohman et al., Proc. Nat'l. Acad. Sci. USA 85: 8998–9002 (1988)) in 30 cycles (denaturation for 30 s at 94° C., annealing for 1 min at 55° C., extension for 2 min at 72° C.; initial denaturation was for 4 min at 94° C., final extension was for 10 min at 72° C.), using the primers

[SEQ ID NO 5]
GCCTTCGAAT TCAGCACCGA GGGAAGTTAC GCTTA 35 and

[SEQ ID NO 6]
GCCTTCGAAT TCAGCACCAA AAAAAAAAAA AAAAA 35

The products were further amplified in a second set of 30 cycles (conditions see above), using the adapter primer

GCCTTCGAAT TCAGCACC 18    [SEQ ID NO 8]

After digestion with EcoRI, the PCR-products were cloned into the EcoRI site of λZAPII (Stratagene) following the manual of the manufacturer. $10^3$ plaques were screened with an internal oligonucleotide probe

AAAAAAAAA(T/A) (T/G)GCCGGGCGC GGT 23    [SEQ ID NO 9]

and 6 positive clones were sequenced.

For amplification of the 3' BC200 sequence, 10 μg total RNA from human neocortex were A-tailed using poly A polymerase (DeChiara et al., 1987). Tailed RNA was then converted into first strand cDNA with reverse transcriptase in the presence of MeHgOH (Invitrogen), using the primer

[SEQ ID NO 10]
GCCTTCGAAT TCAGCACCTT TTTTTTTTT TTTTT 35

This primer, in combination with the primer

[SEQ ID NO 11]
GCCTTCGAAT TCAGCACCAA AATAAGCGTA ACTTCCC 37 was also used for PCR-amplification (see above). Products were cloned into λZAPII (see above), and 14 clones that were identified with SEQ ID NO 11 were sequenced using the enzymatic chain termination reaction.

EXAMPLE 3

Production of BC200 RNA Specific Probe

Two types of probes have routinely been used. In the first example, an oligodeoxynucleotide of the desired sequence was chemically synthesized and purified by chromatography or gel electrophoresis. The oligonucleotide was then radiolabeled by phosphorylation of the 5' end. This was achieved by using the enzyme polynucleotide kinase with $\gamma^{32}P$-labeled ATP. The radiolabeled probe (specific activity: $>10^8$ cpm/μg) was separated from unincorporated label by gel filtration, and the probe was used at a concentration of $10^6$ cpm/ml.

In the second example, RNA probes were generated by in vitro transcription. In this approach, the desired sequence was first cloned into a suitable transcription vector (e.g., pBluescript). This vector was then linearized (so that transcription would terminate at a desired location), and RNA was transcribed from such linearized templates, using SP6, T3, or T7 RNA polymerase. $^{35}S$- or $^3H$-UTP was present during the transcription reaction, and the resulting probes were thus $^{35}S$- or $^3H$-labeled. Template DNA was then digested with DNase I, proteins were phenol-extracted, and the probes were ethanol-precipitated. RNA probes were frequently used for in situ hybridization experiments.

EXAMPLE 4

Evaluation of BC200 RNA in Human Tissues

Human biopsy material was obtained that included the tumor tissue itself and adjacent normal tissue from the same organ. Tumor tissue and normal tissue were separated and frozen until further processing. RNA was extracted from such tissue, using the guanidine thiocyanate method in combination with CsCl-density centrifugation (Feramisco et al., 1982, J. Biol. Chem. 257: 11024–11031).

For Northern hybridization analysis, 10 μg of total RNA (per sample) were run on a 1.5% agarose gel in the presence of 2.2M formaldehyde. RNA was transferred to Gene Screen membranes (NEN) and immobilized by UV-illumination. BC200 RNA was detected on such blots by using a probe that recognizes 30 nucleotides in the 3' unique region of BC200 RNA. (SEQ ID NO 3) Hybridization was at 42° C. Filters were washed in 0.5×SSC, 0.1% SDS, at 50° C., and exposed for autoradiography.

Figure 1A:
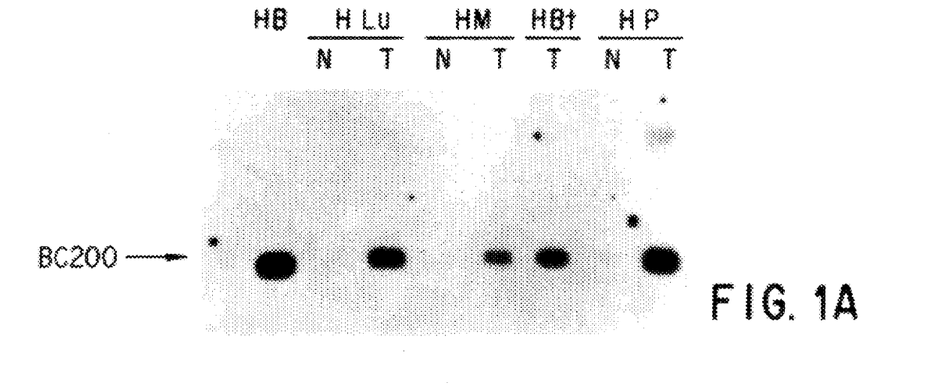
FIGS. 1A, 1B, 2A and 2B show the results of Northern Blot experiments to detect BC200 RNA in various human tissues.
Figure 1B:
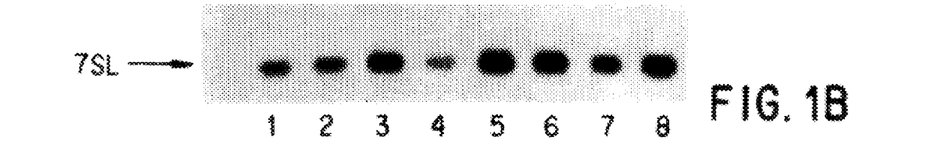
Figure 2A:
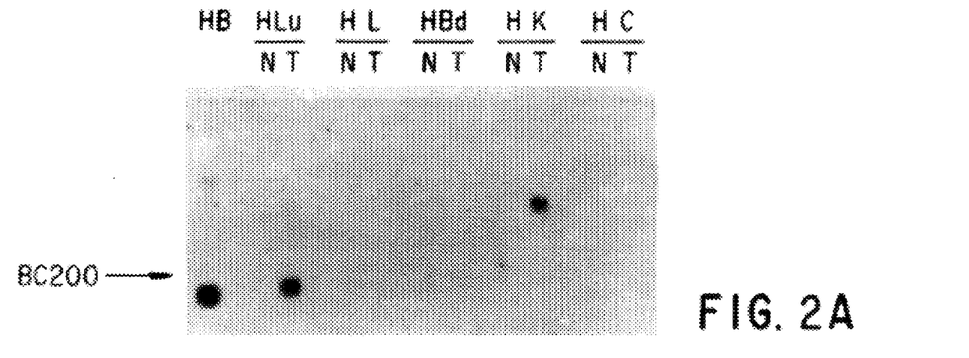
Figure 2B:
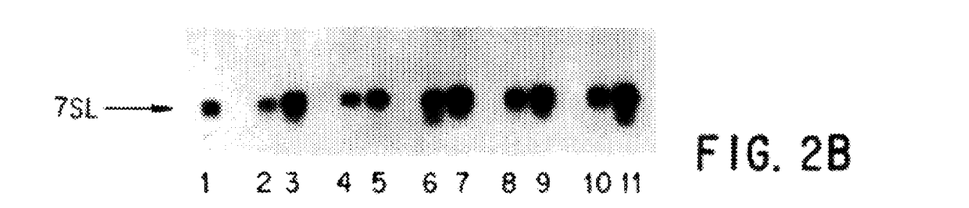

The results of these experiments are shown in FIGS. 1A, 1B, 2A and 2B. FIG. 1A and 1B reveal expression levels in a variety of tumor and corresponding normal tissues of BC200 RNA (FIG. 1A) and of 7SL RNA (FIG. 1B) 7SL RNA was monitored as a control RNA that is ubiquitously expressed by all cell types. Abbreviations: HB, human brain (normal tissue, loaded as a positive control); HLU, human lung (squamous cell carcinoma); HM, human lung metastatic melanoma; HBt, human breast tumor (adenocarcinoma); HP, human parotid carcinoma; T, tumor tissue; N, adjacent normal tissue from the same organ. Note that in the examples shown in FIGS. 1A, and 1B, BC200 RNA is strongly expressed in non-neural tumor tissue and is at the same time undetectable in the corresponding normal tissue. FIGS. 2A and 2B includes examples of tumors that do not express BC200 RNA. Abbreviations: HB, human brain (as in FIGS. 1A and 1B); HLu, human lung (squamous cell carcinoma, as in FIGS. 1A and 1B); HL, human liver tumor; HBd, human bladder carcinoma; HK, human kidney carcinoma; HC, human colon carcinoma. In situ hybridization experiments have confirmed that in BC200-positive tumors, the RNA is expressed by tumor cells, not however by neighboring non-malignant cells (e.g., stroma cells, inflammatory cells).

A summary of the experimental data on the expression of BC200 RNA in various human tumors is given in Table 1. The symbols +, ++ and +++ reflect increasing levels of RNA detected. Especially noteworthy is the patient-to-patient consistency of the data: mammary adenocarcinoma tissue has been shown to express high levels of BC200 RNA in five different patients, while, for example, colon adenocarcinomas were never found to be positive in this assay. This points to the ability of BC200 RNA to act as a broad spectrum marker for a variety of tumors and neoplastic diseases.

TABLE 1

EXPRESSION OF BC200 RNA IN DIFFERENT HUMAN TUMOR TISSUES AND DIFFERENT CELL TYPES

| TISSUE SOURCE | NO. OF CASES | CELL TYPE | BC200 EXP. |
|---|---|---|---|
| HYPOPHARYNX | 1 | EPITHELIAL TUMOR | – |
| TONGUE | 1 | SQUAMOUS CELL CARCINOMA | + |
| ESOPHAGUS | 1 | EPITHELIAL CARCINOMA | + |
| STOMACH | 2 | ADENOCARCINOMA | – |
|  | 1 | TUBULAR ADENOCARCINOMA | + |
| LIVER | 4 |  | – |
| RECTOSIGMOID COLON | 2 | ADENOCARCINOMA | – |
| HEMICOLECTOMY | 1 | ADENOCARCINOMA | – |

TABLE 1-continued

EXPRESSION OF BC200 RNA IN DIFFERENT HUMAN TUMOR TISSUES AND DIFFERENT CELL TYPES

| TISSUE SOURCE | NO. OF CASES | CELL TYPE | BC200 EXP. |
|---|---|---|---|
| COLON | 5 | ADENOCARCINOMA | − |
| KIDNEY & ADRENAL GLAND | 1 | CLEAR CELL | − |
| BLADDER | 1 | TRANSITIONAL | − |
| BREAST | 5 | ADENOCARCINOMA | +++ |
| LUNG | 1 | SQUAMOUS | +++ |
|  | 2 | ADENOCARCINOMA | − |
| PAROTID GLAND | 1 | MUCOEPIDERMOID | +++ |
| THYROID GLAND | 1 |  | − |
| MUSCLE & SKIN | 1 | SARCOMA | + |
| LUNG METASTASIS (MELANOMA) | 1 | MELANOMA | ++ |
| OVARIAN | 1 | PAPILLARY CARCINOMA | + |
| CERVIX | 1 | ENDOTHIAL ADENOCARCINOMA | + |
| NON-HODGKIN LYMPH. | 1 | T CELL TYPE | − |

---

We claim:

1. An oligonucleotide probe which specifically hybridizes to a human BC200 RNA molecule in a region having the sequence set forth for residues 156–185 of SEQUENCE ID NO 1 but which does not hybridize to a human Alu element.

2. An oligonucleotide probe according to claim 1, wherein the probe has the sequence:

TTGTTGCTTT GAGGGAAGTT ACGCTTATTT 30. [SEQ ID NO 3]

3. An oligonucleotide probe according to claim 1, wherein the probe has the sequence:

TTTGAGGGAA GTTACGCTTA T 21. [SEQ ID NO 7]

4. An oligonucleotide probe according to claim 1, further comprising a detectable label.

5. An oligonucleotide probe according to claim 4, wherein the label is a radioactive, chemiluminescent, fluorescent or chromogenic label.

6. An oligonucleotide probe, which specifically hybridizes to a human BC200 RNA molecule in a region having the sequence set forth for residues 156–185 of SEQUENCE ID NO 1 and (2) does not hybridize to a human BC200 RNA molecule in the region having the sequence set forth for residues 1–122 of SEQ ID NO 1.

7. An oligonucleotide probe which (i) specifically hybridizes to a cDNA transcript of a human BC200 RNA molecule, a portion of which RNA molecule has the sequence set forth for residues 156–185 of SEQUENCE ID NO 1 but (ii) does not hybridize to a human Alu element.

8. A method of screening human breast tissue for the presence of adenocarcinoma comprising the steps of:

(a) obtaining a sample of human breast tissue;

(b) preparing the test sample such that RNA in the test sample is capable of reacting with a detection reagent; and (c) combining the test sample with the detection reagent under conditions that produce a detectable reaction product if BC200 RNA is present; wherein detectable reaction product in the test sample has a positive correlation with the presence of breast adenocarcinoma.

* * * * *

UNITED STATES PATENT AND TRADEMARK OFFICE
CERTIFICATE OF CORRECTION

PATENT NO. : 5,670,318

DATED : September 23, 1997

INVENTOR(S) : Henri Tiedge; Jurgen Brosius

It is certified that error appears in the above-identified patent and that said Letters Patent is hereby corrected as shown below:

Col. 3, line 6
"GAGGGAGTT" should read

--GAGGGAAGTT--;

Col. 3, line 57
"[α-$^{32}$p]dNTps" should read --[α-$^{32}$P] dNTPs.--.

Signed and Sealed this

Sixteenth Day of February, 1999

Attest:

Attesting Officer

*Acting Commissioner of Patents and Trademarks*

UNITED STATES PATENT AND TRADEMARK OFFICE
CERTIFICATE OF CORRECTION

| | | |
|---|---|---|
| PATENT NO. | : 5,670,318 | Page 1 of 1 |
| APPLICATION NO. | : 08/438500 | |
| DATED | : September 23, 1997 | |
| INVENTOR(S) | : Henri Tiedge and Jurgen Brosius | |

It is certified that error appears in the above-identified patent and that said Letters Patent is hereby corrected as shown below:

Please replace the paragraph beginning at Col. 1, line 14 and ending at Col. 1, line 17 with the following paragraph:

-- This invention was made with government support under grant number MH38819 awarded by the National Institutes of Mental Health. The United States Government has certain rights in the invention. --

Signed and Sealed this

Twenty-second Day of September, 2009

David J. Kappos
*Director of the United States Patent and Trademark Office*

SEQUENCE LISTING ( 1 ) GENERAL INFORMATION:

( i i i ) NUMBER OF SEQUENCES: 13

( 2 ) INFORMATION FOR SEQ ID NO: 1:

( i ) SEQUENCE CHARACTERISTICS:
        ( A ) LENGTH: 200
        ( B ) TYPE: nucleic acid
        ( C ) STRANDEDNESS: single
        ( D ) TOPOLOGY: linear     ( i i ) MOLECULE TYPE: mRNA     ( i i i ) HYPOTHETICAL: no     ( i v ) ANTI-SENSE: no     ( v i ) ORIGINAL SOURCE:
        ( A ) ORGANISM: human
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE: neocortex
        ( G ) CELL TYPE:
        ( H ) CELL LINE:
        ( I ) ORGANELLE:

( i x ) FEATURE:
        ( A ) NAME/KEY: human BC200 RNA     ( x i ) SEQUENCE DESCRIPTION: SEQ ID NO: 1:

```
GGCCGGGCGC  GGUGGCUCAC  GCCUGUAAUC  CCAGCUCUCA  GGGAGGCUAA  GAGGCGGGAG      60

GAUAGCUUGA  GCCCAGGAGU  UCGAGACCUG  CCUGGGCAAU  AUAGCGAGAC  CCCGUUCUCC     120

AGAAAAAGGA  AAAAAAAAA   CAAAAGACAA  AAAAAAAAUA  AGCGUAACUU  CCCUCAAAGC     180

AACAACCCCC  CCCCCCCUUU                                                    200
```

( 2 ) INFORMATION FOR SEQ ID NO: 2:

( i ) SEQUENCE CHARACTERISTICS:
  ( A ) LENGTH: 42
  ( B ) TYPE: nucleic acid
  ( C ) STRANDEDNESS: single
  ( D ) TOPOLOGY: linear ( i i ) MOLECULE TYPE: MRNA ( i i i ) HYPOTHETICAL: no ( i v ) ANTI-SENSE: no ( v i ) ORIGINAL SOURCE:
  ( A ) ORGANISM: human
  ( B ) STRAIN:
  ( C ) INDIVIDUAL ISOLATE:
  ( D ) DEVELOPMENTAL STAGE:
  ( E ) HAPLOTYPE:
  ( F ) TISSUE TYPE: neocortex
  ( G ) CELL TYPE:
  ( H ) CELL LINE:
  ( I ) ORGANELLE:

( i x ) FEATURE:
  ( D ) OTHER INFORMATION: unique sequence from human BC200 RNA ( x i ) SEQUENCE DESCRIPTION: SEQ ID NO: 2:

UAAGCGUAAC UUCCCUCAAA GCAACAACCC CCCCCCCCU UU        42

( 2 ) INFORMATION FOR SEQ ID NO: 3:

( i ) SEQUENCE CHARACTERISTICS:
  ( A ) LENGTH: 30
  ( B ) TYPE: nucleic acid
  ( C ) STRANDEDNESS: single
  ( D ) TOPOLOGY: linear ( i i ) MOLECULE TYPE: other nucleic acid ( i i i ) HYPOTHETICAL: no ( i v ) ANTI-SENSE: yes ( v i ) ORIGINAL SOURCE:
  ( A ) ORGANISM:
  ( B ) STRAIN:
  ( C ) INDIVIDUAL ISOLATE:
  ( D ) DEVELOPMENTAL STAGE:
  ( E ) HAPLOTYPE:
  ( F ) TISSUE TYPE:
  ( G ) CELL TYPE:
  ( H ) CELL LINE:
  ( I ) ORGANELLE:

( i x ) FEATURE:
  ( D ) OTHER INFORMATION: probe for unique sequence from human
    BC200 RNA ( x i ) SEQUENCE DESCRIPTION: SEQ ID NO: 3:

TTTATTCGCA TTGAAGGGAG TTTCGTTGTT        30

( 2 ) INFORMATION FOR SEQ ID NO: 4:

( i ) SEQUENCE CHARACTERISTICS:
  ( A ) LENGTH: 19
  ( B ) TYPE: nucleic acid
  ( C ) STRANDEDNESS: single
  ( D ) TOPOLOGY: linear ( i i ) MOLECULE TYPE: other nucleic acid ( i i i ) HYPOTHETICAL: no ( i v ) ANTI-SENSE: no ( v i ) ORIGINAL SOURCE:

(A) ORGANISM:
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(D) OTHER INFORMATION: primer for human BC200 RNA (xi) SEQUENCE DESCRIPTION: SEQ ID NO: 4:

GTTGTTGCTT TGAGGGAAG        19

(2) INFORMATION FOR SEQ ID NO: 5:

(i) SEQUENCE CHARACTERISTICS:
(A) LENGTH: 35
(B) TYPE: nucleic acid
(C) STRANDEDNESS: single
(D) TOPOLOGY: linear (ii) MOLECULE TYPE: other nucleic acid (iii) HYPOTHETICAL: no (iv) ANTI-SENSE: no (vi) ORIGINAL SOURCE:
(A) ORGANISM:
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(D) OTHER INFORMATION: amplification primer for t-tailed human
BC200 cDNA (xi) SEQUENCE DESCRIPTION: SEQ ID NO: 5:

GCCTTCGAAT TCAGCACCGA GGGAAGTTAC GCTTA        35

(2) INFORMATION FOR SEQ ID NO: 6:

(i) SEQUENCE CHARACTERISTICS:
(A) LENGTH: 35
(B) TYPE: nucleic acid
(C) STRANDEDNESS: single
(D) TOPOLOGY: linear (ii) MOLECULE TYPE: other nucleic acid (iii) HYPOTHETICAL: no (iv) ANTI-SENSE: no (vi) ORIGINAL SOURCE:
(A) ORGANISM:
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(D) OTHER INFORMATION: amplification primer for t-tailed human
BC200 cDNA ( x i ) SEQUENCE DESCRIPTION: SEQ ID NO: 6:

GCCTTCGAAT TCAGCACCAA AAAAAAAAA AAAAA    35

( 2 ) INFORMATION FOR SEQ ID NO: 7:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear     ( i i ) MOLECULE TYPE: other nucleic acid     ( i i i ) HYPOTHETICAL: no     ( i v ) ANTI-SENSE: yes     ( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( i x ) FEATURE:
        ( D ) OTHER INFORMATION: probe for detection of BC200 RNA     ( x i ) SEQUENCE DESCRIPTION: SEQ ID NO: 7:

TATTCGCATT GAAGGGAGTT T    21

( 2 ) INFORMATION FOR SEQ ID NO: 8:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear     ( i i ) MOLECULE TYPE: other nucleic acid     ( i i i ) HYPOTHETICAL: no     ( i v ) ANTI-SENSE: no     ( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( i x ) FEATURE:
        ( D ) OTHER INFORMATION: amplification primer for BC200RNA     ( x i ) SEQUENCE DESCRIPTION: SEQ ID NO: 8:

GCCTTCGAAT TCAGCACC    18

( 2 ) INFORMATION FOR SEQ ID NO: 9:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: no ( i v ) ANTI-SENSE: no ( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( i x ) FEATURE:
    ( D ) OTHER INFORMATION: amplification primer for BC200RNA ( x i ) SEQUENCE DESCRIPTION: SEQ ID NO: 9:

```
AAAAAAAAN NGCCGGGCGC GGT                                       23
```

( 2 ) INFORMATION FOR SEQ ID NO: 10:

( i ) SEQUENCE CHARACTERISTICS:
        ( A ) LENGTH: 35
        ( B ) TYPE: nucleic acid
        ( C ) STRANDEDNESS: single
        ( D ) TOPOLOGY: linear     ( i i ) MOLECULE TYPE: other nucleic acid     ( i i i ) HYPOTHETICAL: no     ( i v ) ANTI-SENSE: no     ( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( i x ) FEATURE:
        ( D ) OTHER INFORMATION: amplification primer for BC200RNA     ( x i ) SEQUENCE DESCRIPTION: SEQ ID NO: 10:

```
GCCTTCGAAT TCAGCACCTT TTTTTTTTT TTTTT                          35
```

( 2 ) INFORMATION FOR SEQ ID NO: 11:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear     ( i i ) MOLECULE TYPE: other nucleic acid     ( i i i ) HYPOTHETICAL: no     ( i v ) ANTI-SENSE: no     ( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:

( H ) CELL LINE:
( I ) ORGANELLE:

( i x ) FEATURE:
( D ) OTHER INFORMATION: amplification primer for BC200RNA ( x i ) SEQUENCE DESCRIPTION: SEQ ID NO: 11:

GCCTTCGAAT TCAGCACCAA AATAAGCGTA ACTTCCC 37

( 2 ) INFORMATION FOR SEQ ID NO: 12:

( i ) SEQUENCE CHARACTERISTICS:
( A ) LENGTH: 22
( B ) TYPE: nucleic acid
( C ) STRANDEDNESS: single
( D ) TOPOLOGY: linear ( i i ) MOLECULE TYPE: other nucleic acid ( i i i ) HYPOTHETICAL: no ( i v ) ANTI-SENSE: yes ( v i ) ORIGINAL SOURCE:
( A ) ORGANISM:
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( D ) OTHER INFORMATION: probe for BC200RNA ( x i ) SEQUENCE DESCRIPTION: SEQ ID NO: 12:

CCTCTTAGCC TCCCTGAGAG CT 22

( 2 ) INFORMATION FOR SEQ ID NO: 13:

( i ) SEQUENCE CHARACTERISTICS:
( A ) LENGTH: 20
( B ) TYPE: nucleic acid
( C ) STRANDEDNESS: single
( D ) TOPOLOGY: linear ( i i ) MOLECULE TYPE: other nucleic acid ( i i i ) HYPOTHETICAL: no ( i v ) ANTI-SENSE: NO ( v i ) ORIGINAL SOURCE:
( A ) ORGANISM:
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( D ) OTHER INFORMATION: amplification primer for BC200RNA ( x i ) SEQUENCE DESCRIPTION: SEQ ID NO: 13:

CCAGCTCTCA GGGAGGCTAA 20